United States Patent
Black et al.

[19]

[11] Patent Number: 6,076,395
[45] Date of Patent: Jun. 20, 2000

[54] CONSTANT STRESS DIFFUSION CELL WITH CONTROLLABLE MOISTURE CONTENT

[75] Inventors: Patrick B. Black, Liberty Corner, N.J.; Timothy Andrew Hansen, Raleigh, N.C.; Robert H. Anderson, Fitzwilliam, N.H.

[73] Assignee: The United States Army Corps of Engineers as represented by the Secretary of the Army, Washington, D.C.

[21] Appl. No.: 09/018,968
[22] Filed: Feb. 5, 1998
[51] Int. Cl.[7] .................................................. G01N 13/04
[52] U.S. Cl. ............................................................ 73/64.47
[58] Field of Search ........................ 73/64.47, 61.41, 73/38

[56] References Cited

U.S. PATENT DOCUMENTS

| 2,345,935 | 4/1944 | Hassler | 73/38 |
| 2,534,718 | 12/1950 | Leas et al. | 73/38 |
| 3,367,850 | 2/1968 | Johnson | 73/61.43 |

*Primary Examiner*—Daniel S. Larkin
*Attorney, Agent, or Firm*—Luther A. Marsh

[57] ABSTRACT

A device for measuring the concentration changes of a vapor at various moisture contents ranging from saturation to dry and under different confining stress as it diffuses through a porous media which includes a porous central housing having a central space and a fluid conveying line extending into the central space of the central housing and an outer housing which encompasses for containment of the central housing and is positioned in an outward spaced relation from the central housing to form a medial space, between the external housing and the internal housing and having a second fluid conveying line extending into the medial space.

24 Claims, 1 Drawing Sheet

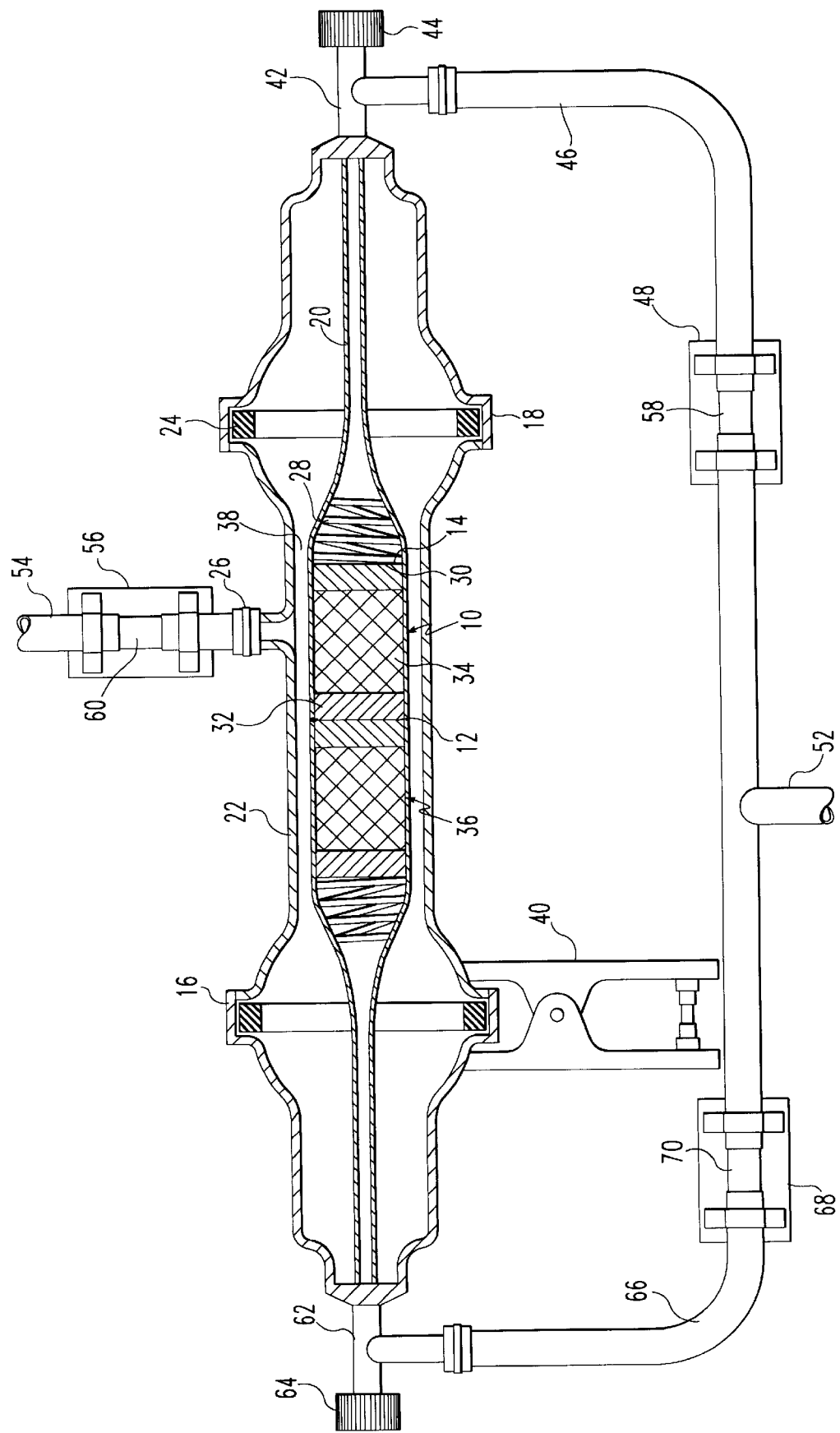

CONSTANT STRESS DIFFUSION CELL WITH CONTROLLABLE MOISTURE CONTENT

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates to methods and apparatus for testing and measurement and more particularly to methods and apparatus for measuring vapor penetration through a porous media.

(2) Brief Description of the Prior Art

The prior art discloses a variety of ways of using a diffusion cell to monitor vapor penetration.

U.S. Pat. No. 4,548,072 to McAndless, for example, discloses a device for monitoring the penetration of vapor from a challenge liquid occluded by a garment material, through the garment material, wherein pressure is applied against the garment material. The vapor which penetrates through the garment material is picked up by an inert carrier gas and detected to determine the protection afforded by the garment material against penetration by the challenge liquid/vapor.

U.S. Pat. No. 4,958,529 to Vestal discloses a gas diffusion cell having a membrane therein separating the cell into an aerosol flow chamber and a sweep gas flow chamber. The effluent is sprayed as an aerosol into the aerosol flow chamber, and vaporized solvent diffuses through the gas membrane into the sweep gas flow chamber while particles of interest are output to the detector. Sweep gas is passed through the sweep gas flow chamber for removing the solvent vapor, and the flow rate of sweep gas is controlled to achieve little or no net flow of gas across the membrane.

U.S. Pat. No. 5,005,403 to Steudle et al. discloses a process for determining the concentration of a substance dissolved in a solvent by means of an osmometer. The osmometer comprises a two-chamber system with a first chamber having an osmosis cell and a second chamber for the measurement solution. The pressure in the osmosis cell is held constant with an incompressible membrane arrangement.

To summarize the prior art, known methods to determine the diffusion coefficient of a vapor through a porous media are generally either for thin membranes or dry and friable media. With particular regard to the soil science and engineering disciplines, diffusion across thin membranes are known. In the soil science and engineering disciplines, however, diffusion coefficients are generally determined for loosely packed soils that tend to be at near dry conditions.

A need, therefore, exists for a method and apparatus measuring the diffusion coefficient of a vapor through a porous material which compensates for differences in moisture content and confining stress in the porous media. A need, in particular, exists for such a method and apparatus which is adapted for use on soils and other similar porous materials.

SUMMARY OF THE INVENTION

The method and apparatus of this invention measures the concentration changes of a vapor as it diffuses through a porous media. The diffusion coefficient for the vapor in the porous media is then calculated from the measured concentration changes with time. In addition, the device presented in this invention provides the capability to control both the moisture content and the confining stress. The changes in the diffusion coefficient arising from changes in water content and bulk density are then easily calculated from data collected with the device under the required test conditions. This invention provides a simple method to measure the effective diffusion coefficient for a vapor in a porous media at various moisture contents ranging from saturation to dry and under different confining stress.

The invention comprises a device for measuring the concentration changes of a vapor as it diffuses through a porous media which includes a porous central housing having a central space. An outer housing is positioned in outward spaced relation from the central housing to form a medial space between said external housing and the internal housing. A fluid conveying line with a volume monitor extends into the central space of the central housing. A second fluid conveying line with a volume monitor extends to the medial space. The first fluid conveying line is connected to a pressure regulator line. Preferably, there is a third fluid conveying line which is also connected to the pressure regulator line.

BRIEF DESCRIPTION OF THE DRAWING

Other objects, features, and advantages of the present invention will become apparent upon reference to the following description of the preferred embodiment and to the drawing, wherein corresponding reference characters indicate corresponding parts throughout the several views of the drawings and wherein:

The FIGURE is a cut away schematic view of a device which represents a preferred embodiment of the present invention.

DETAILED DESCRIPTION OF THE PREFERRED EMBODIMENT

Referring to the drawing, the device of the present invention consists of a central cylindrical cell comprised of a porous cylinder 10 with opposed open ends 12 and 14 that are covered respectively by two end caps 16 and 18 that contain access ports as at port 20. This central cylinder is surrounded by another outer cylinder 22 that is sealed to the endcaps 16 and 18 by appropriate gaskets as at gasket 24 and provides access to the exterior through an outer cylinder access port 26. Inside each endcap 16 and 18 is a confining spring as at spring 28 that maintains proper confining stress by pressing against a rigid porous mesh 30. A second power cylinder 36 is positioned adjacent to and aligned with cylinder 10.

The pore size of the porous cylinder 10 must be small enough to assure liquid saturation throughout the test. The pore size of the rigid porous mesh 30 and 32, on the other hand, must be large enough so as not to influence the diffusion of the vapor, but small enough to contain the porous material 34 which is housed in the central space of cylinder 10. This second cylinder 36 is essentially identical to and aligned with cylinder 10 and has porous material interposed between two porous meshes. It will be understood that another spring presses against a rigid porous mesh on the other side of cylinder 36.

To assemble the device, the porous material 34 is packed inside the central space of porous cylinder 10 to the appropriate density. The sample can be wet or dry, but better results might be obtained with a slurry for a loose granular material or saturation for a rigid porous media. The sample is then bounded by the rigid porous mesh 30 and 32 and the endcaps 16 and 18 with the confining spring as at 28, and sealed to the porous cylinder 10 with appropriate gaskets as at gasket 24. The gaskets as at gasket 241 might be O-rings if the porous cylinder 10 is machinable, otherwise, simple flat rings or formable gasket material. A piston controlled system may by substituted for the simple spring 28.

The central assembly is inserted into the outer cylinder 22 and again appropriately sealed with gaskets 24 to the endcaps 16 and 18. In its present configuration, the endcaps 16 and 18 and the outer cylinder 22 are held together with a clamp 40. The medial space 38 between the inside of the outer cylinder 22 and the outside of the central cylinders 10 and 36 is liquid filled which is accomplished by performing this assembly stage submerged in the liquid. The final stage in the assembly process is to connect the input and output ports to suitable connections. In this present configuration, the access port 20 on the endcap 18 is connected to a T-connector 42 that is in turn connected to a sampling port 44 and a vapor line 46 having an inline monitor 48 which is downstream of the pressure regulator line 52. The access port 26 on the outer cylinder 22 is also connected by the liquid line 54 to the inline monitor 56. In an inline monitor 48 there is a liquid drop 58. In the inline monitor 56 there is a vapor bubble 60. Adjacent the endcap 16 there is a T-connector 62 connecting to a sampling port 64 and vapor line 66 which connects to pressure regulator line 52. There is an inline monitor 63 in which there is a liquid drop 70. The end cap 16 is held in position by a spring (not shown) in the same way as end cap 18.

Volume changes in the head space vapor and the water content of the porous media 34 are measured with inline monitors 48, 56, and 68. In the case of the endcaps 16 and 18, the drop of liquid 60 inside the vapor line 54 acts as a barrier between the vapor in the endcap 16 and the confining vapor from the pressure regulator line 52. The volume change in headspace is then determined by monitoring the movement of the menisci. Similarly, the liquid vapor menisci 58 and 70 in the inline monitors 48 and 68 on the outer cylinder 22 determines the total volume of liquid displaced from the porous media. The above described apparatus may be operated by one of the following methods:

1) by pressurizing the vapor in the endcaps 16 and 18 through the access ports as at port 20, and 2) by pressurizing the liquid through the output port 26.

In the first case, the endcaps 16 and 18 are connected to a pressure regulated line 52 through the inline monitors 48 and 68. As the pressure is increased, fluid within the porous media 34 is pushed through the porous cylinder 10. On the side of the pressures regulated line 52, the menisci on the liquid drops 58 and 70 in the inline monitors 48 and 68 moves toward the apparatus indicating a decreased volume change while the fluid, discharged the porous media 34 is registered as a volume increase on the inline monitor 56 connected to the output port 26. When the system is stabilized and no further volume changes are observed, a diffusion coefficient measurement is taken.

The diffusion coefficient is determined by monitoring concentration changes with time of a vapor as it diffuses through the porous media 34 from an endcap 16 containing a higher concentration of the vapor to the lower concentration endcap 18. The vapor can be the same as that already contained within the system or it can be an additional vapor. For example, if the porous media were a soil, then the confining vapor might be air and the diffusing vapor a trace volatile compound. In this case, the trace volatile compound is injected into one endcap 18 through its sampling port 44. Samples would then be obtained by removing small volume samples with time from the opposite endcap 16 through its sampling port 64 and possibly from the originally spiked endcap 16.

The collected concentration change with time data represents a breakthrough curve for the vapor in the porous media 34 at a given moisture content and confining stress. These data are then used to solve Fick's second law of diffusion for the effective diffusion coefficient. The appropriate solution will depend upon the boundary conditions. If the concentration of the injected vapor is large enough that its concentration does not significantly change during the test, then it might be assumed to be a constant and thus simplify to an analytic solution. A more general solution would include time varying concentrations in both endcaps 16 and 18 and thus most likely lead to a numerical solution based upon the measured data.

Those skilled in the art will appreciate that the method and apparatus of this invention allows for both moisture content and confining stress control of the porous media. Diffusion coefficients can be determined for the whole range of moisture contents ranging from the standard dry condition to saturation, granted that a saturated porous media should have no vapor diffusion, but it might have adsorption and partitioning. Furthermore, the impact of confining stress on the porous media is also measurable. An example of this factor is the change of diffusion coefficient for the same porous media as its pore size distribution is changed with change in confining stress.

The diffusion of vapors through porous media is controlled by the pore space geometry of the porous media. This geometry is strongly impacted by the presence of moisture and the changes arising from alterations in the mechanical confining stress. In soils, for example, an increase in water content will greatly reduce the diffusion coefficient of a vapor. Likewise, the same soil will also display a decrease in diffusion coefficient if the soil is compressed. The method and apparatus of this invention provides a simple method to control both the confining stress and moisture content of a porous media while allowing its diffusion coefficient to be determined for the given conditions. Both rigid, rock cores, ceramics and medical pills, and friable, sands and starches, porous media are handled with this invention allowing for its wide applicability. It will also be appreciated that the diffusion coefficient of any vapor through any porous media is measured by the apparatus presented in this patent. All samples sizes and confining pressures are handled by this approach. Specific engineering and material properties of the apparatus are left to the end user. Likewise, any moisture content ranging from dry to saturated for any liquid of interest is possible, again the necessary material properties of the apparatus are left to the end user.

Finally, it will also be understood that the method and apparatus of this invention affords the user the ability to handle the full span of moisture contents ranging from dry to saturation as well as to control the confining stress of the porous media. Both of these features make this method and apparatus useful in many applications ranging from determining the vapor diffusion of a volatile organic compound through the vadose zone in soil to the diffusion of trace vapors through porous ceramics and metals.

While the present invention has been described in connection with the preferred embodiments of the various elements, it is to be understood that other similar embodiments may be used or modifications and additions may be made to the present described embodiment for performing the same function of the present invention without deviating therefrom. Therefore, the present invention should not be limited to any single embodiment, but rather construed in breadth and scope in accordance with the recitation of the appended claims.

What is claimed is:

1. A device for measuring the concentration changes of a vapor as it diffuses through a porous media comprising:
   a porous central housing having a central space;
   an outer housing for containment of an internal housing and being positioned in an outward spaced relation from the central housing to form a medial space between an external housing and said internal housing;
   a first fluid convenying line extending into the central space of the central housing and having a first volume monitoring means; and
   a second fluid conveying line extending into the medial space.

2. The device of claim 1 wherein the second fluid conveying line has a second volume monitoring means.

3. The device of claim 2 wherein there is an access port in the internal housing and the first fluid conveying line connects to said access port.

4. The device of claim 3 wherein the central housing has at least one opening covered by a cap and the access port is in said cap.

5. The device of claim 4 wherein the cap is scaled to the outer housing.

6. The device of claim 5 wherein means are provided for restraining the cap against movement from the central housing.

7. The device of claim 6 wherein the means provided for restraining the cap against movement from the central housing comprises a spring.

8. The device of claim 4 wherein a rigid porous mesh is interposed between the central housing and the cap.

9. The device of claim 3 wherein the central housing is cylindrical having opposed openings.

10. The device of claim 9 wherein opposed caps cover the opposed openings.

11. The device of claim 2 wherein a vapor sampling line intersects the first fluid line outside the central housing.

12. The device of claim 11 wherein the vapor sampling line intersects the first fluid line downstream from the first volume monitoring means.

13. The Crevice of claim 12 wherein a pressure regulation means is provided upstream from the first volume monitoring means.

14. The device of claim 3 wherein there is a second access port in the outer housing and the second fluid-conveying line connects to said second access port.

15. The device of claim 2 wherein the porous media is contained in the central space of the internal housing.

16. The device of claim 15 wherein a liquid is contained in the medial space.

17. The device of claim 16 wherein the liquid is also included with the porous medial in the central space of the internal housing.

18. The device of claim 17 wherein the first fluid conveying line contains a gas.

19. The device of claim 18 wherein the second fluid conveying line contains a liquid.

20. A device for measuring the concentration changes of a vapor as it diffuses through a porous media comprising:
   a porous central housing having a central space;
   an outer housing for containment of an internal housing and being positioned in outward spaced relation from the central housing to form a medial space between said external housing and said internal housing;
   a pressure regulating means;
   a first fluid conveying line extending from the pressure regulating means into the central space of the central housing and having a volume monitoring means and a vapor sampling means;
   a second fluid conveying line extending into the medial space and having a volume monitoring means; and
   a third conveying line extending from the pressure regulating means into the central space of the central housing and having a volume monitoring means and a vapor sampling means.

21. The device of claim 20 wherein first fluid conveying means and the third fluid conveying means contain a vapor.

22. The device of claim 21 wherein the second fluid conveying means contains a liquid.

23. The device of claim 22 wherein the volume monitoring means in the first fluid conveying means and the third fluid conveying means comprises a drop of liquid.

24. The device of claim 23 wherein the volume monitoring means in the second fluid conveying means comprises a vapor bubble.

* * * * *